(12) United States Patent
Scott et al.

(10) Patent No.: US 6,596,338 B2
(45) Date of Patent: Jul. 22, 2003

(54) ANTIBIOTIC CALCIUM PHOSPHATE COATING

(75) Inventors: Christopher Scott, Hackensack, NJ (US); Joseph Zitelli, River Edge, NJ (US); Paul Higham, Ringwood, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 10/001,525

(22) Filed: Oct. 24, 2001

(65) Prior Publication Data

US 2003/0077381 A1 Apr. 24, 2003

(51) Int. Cl.$^7$ ............... B05D 1/00; B05D 1/38; A61L 27/00; A61L 27/32; A61L 27/54
(52) U.S. Cl. ............... 427/2.26; 427/2.1; 427/2.27; 427/2.24; 427/2.14; 427/372.2; 427/402; 427/403
(58) Field of Search ............... 427/2.1, 2.26, 427/2.27, 2.24, 2.14, 372.2, 402, 403

(56) References Cited

U.S. PATENT DOCUMENTS

| | | | |
|---|---|---|---|
| 5,164,187 A | | 11/1992 | Constantz et al. |
| 5,188,670 A | * | 2/1993 | Constantz ............... 118/667 |
| 5,279,831 A | | 1/1994 | Constantz et al. |
| 5,607,685 A | * | 3/1997 | Cimbollek et al. ........ 424/422 |
| 5,679,646 A | * | 10/1997 | Cimbollek et al. ........ 514/43 |
| 5,730,598 A | | 3/1998 | Story et al. |
| 5,733,564 A | * | 3/1998 | Lehtinen ............... 424/423 |
| 5,827,289 A | * | 10/1998 | Reiley et al. ............... 606/86 |
| 5,968,253 A | | 10/1999 | Poser et al. |
| 5,972,368 A | * | 10/1999 | McKay ............... 424/423 |
| 6,346,121 B1 | * | 2/2002 | Hicks et al. ............... 623/6.64 |

OTHER PUBLICATIONS

I. Soriano et al.; Formulation Of Calcium Phosphates/Poly (d,l–lactide) Blends Containing Gentamicin For Bone Implantation; Journal of Controlled Release; 2000; pp. 121–134; vol. 68; Elsevier Science B.V.

H. Gautier et al.; Isostatic Compression, A New Process For Incorporating Vancomycin Into Biphasic Calcium Phosphate: Comparison With A Classical Method; Biomaterials; 2000; pp. 243–249, vol. 21; Elsevier Science Ltd.

Y. Huang et al.; Study On The Applied Properties Of Tobramycin–Loaded Calcium Phosphate Cement, Key Engineering Materials; 2001; pp. 853–860; vol. 192–195; Trans Tech. Publications; Switzerland.

M. Bohner et al.; Gentamicin Sulfate Release From A Hydraulic Calcium Phosphate Cement: Influence of The Additive Poly (Acrylic Acid); Proceed Int'l Symp. Control Rel. Bioact. Mater.; 1997; pp. 1009–1010; vol. 24; Controlled Release Society, Inc.

I–Chung Tung; In Vitro Drug Release Of Antibiotic–Loaded Porous Hydroxyapatite Cement; Art, Cells, Blood Subs., and Immob. Biotech., 1995, pp. 81–88, vol. 23(I), Marcol Dekker, Inc.

J. P. Zitelli et al.; A Novel Method For Solution Deposition Of Hydroxyapatite On To Three Dimensionally Porous Metallic Surface: Peri–Apatite HA; Mat. Res. Soc. Symp. Proc.; vol. 599; 2000 Materials Research Society; pp. 117–128.

A. Ganguli et al; The Interaction of Biophosphonate–coated Hyrdoxyapatite and Osteoblasts; Euro Biomats; Sep., 2001.

* cited by examiner

*Primary Examiner*—Shrive P. Beck
*Assistant Examiner*—Jennifer Kolb Michener
(74) *Attorney, Agent, or Firm*—Lerner, David, Littenberg, Krumholz & Mentlik, LLP

(57) ABSTRACT

A process for applying a coating having a therapeutic agent such as an antibiotic to an implant uses the high surface area of a calcium phosphate coated metal implant as a repository for the therapeutic agent. The implant is coated with one or more layers of calcium phosphate minerals such as hydroxyapatite. After the crystalline layer is applied, which is usually done within an aqueous solution, the implant is dried and packaged. Immediately prior to implantation, the implant is removed from the package and the crystalline layer of calcium phosphate is wetted with an aqueous solution containing the therapeutic agent.

25 Claims, No Drawings

ANTIBIOTIC CALCIUM PHOSPHATE COATING

BACKGROUND OF THE INVENTION

The field of this invention relates to mineralized coatings of prosthetic devices. More particularly the invention relates to a porous calcium phosphate mineral coated prosthesis which includes a coating having a therapeutic agent, such as an antibiotic in water, absorbed therein.

The use of prosthetic devices for treatment of bone injuries/illnesses is continuously expanding with an increasingly active and aging population. The use of bone replacements for bone fractures, removal of bone, or the use of supports for weakened bone requires that the artificial bone replacement form a strong joint or bone with natural bone to insure the integrity of the structure. Bone is able to grow into adjacent structure, particularly where the adjacent structures are porous and compatible with the bone. However, not only must the bone be able to grow into a porous structure, but there must be bonding in a form which allows for a strong bond between the natural ingrown bone and the prosthetic device.

The key requirement for bony fixation of prosthetic implants is that bone grows onto and/or into the implant's surface. A number of studies have shown that calcium phosphate coatings, such as biological apatite, on Cobalt Chrome (Co—Cr) and Titanium (Ti)-alloy implants foster more rapid bony apposition than the bare surfaced alloys alone.

Biological apatite $Ca_{10}(PO_4)_6(OH)_2$ is one of the major compounds occurring in human bones and teeth. A synthetic form of this mineral, hydroxyapatite (HA) is very similar to the natural occurring apatite. This similarity between synthetic HA and naturally occurring apatite has led scientists to pursue the use of HA with dental and orthopedic implants. Coating with HA or other crystalline calcium phosphate produces an implant that readily integrates with surrounding bone and tissue after being implanted.

Some of the first dental and orthopedic implants attempting to employ synthetic apatite were completely formed from sintered or plasma sprayed HA.

Plasma spraying is one process known for coating metallic implants with HA. During this process, a stream of mixed gases passes through a high temperature electric arc that ionizes the gases into a plasma flame. Thereafter, crystalline HA feedstock powder is fed into the stream and then impinged in a molten state onto the outer surface of the implant. The spray adheres to the surface and forms a relatively thin coating of ceramic HA.

HA coated implants exhibit the advantages of both purely metallic implants and purely HA implants. As such, these implants are strong, and bone tissue tends to form a strong bone interface with the surface of the coating and thus promote biocompatibility and osseointegration. Unfortunately, plasma spraying results in several important disadvantages.

Plasma spraying exposes HA to extremely high temperatures that, in turn, induce unwanted changes in morphology and chemical composition. These changes pose particular problems. In particular, it is known that highly crystalline HA has an in vitro stability that is much higher than non-crystalline HA. HA feedstock of a good quality does have a completely crystalline form before it is sprayed. The temperatures associated with plasma spraying, though, cause the HA to partially transform from its pure and crystalline form to one having a much less crystalline structure. This non-crystalline form of HA is commonly referred to as amorphous calcium phosphate (ACP). During plasma spraying, crystalline HA feedstock is also partially converted into other crystalline compounds, such a tricalcium phosphate (TCP including α-TCP and β-TCP), tetracalcium phosphate (TTCP), and calcium oxide (CaO). Collectively, these impurities may be referred to as crystalline soluble phases because their solubility in aqueous solutions is substantially higher than that of crystalline HA. Thus, a process for low temperature deposition of crystalline HA was desired.

SUMMARY OF THE INVENTION

Crystalline calcium phosphate coatings are preferably produced in a low temperature one or multi-step process which provides for a strong adherent uniform thin coating of crystalline hydroxyapatite on a substrate surface, where the coating has long needles or whiskers, which appear to induce bone ingrowth and strong bonding between natural bone and the coating via bone ingrowth and opposition on a pore comprising implant.

The coatings are found to have a high hydroxyapatite $Ca_{10}(PO_4)_6(OH)_2$ surface area because of the fibrous hydroxyapatite crystals. The surface area will generally range from about 1–25m$^2$/cm$^2$ of area. The coatings may be as thin as about 2 µm, preferably being at least about 5 µm (µm=microns), and more preferably at least about 10 µm, and may range to 40 µm thick or greater, depending upon need. Usually, a relatively thin coating will be employed to avoid thick brittle ceramic interfaces between the substrate and the ductile bone. The process taught in U.S. Pat. Nos. 5,164,187 and 5,188,670, the teachings of which are incorporated herein by reference, may produce such coatings.

The single crystals or whiskers, which are produced by the method of U.S. Pat. No. 5,164,187, will generally range from about 0.01 microns to 20 microns in diameter and about 1 micron to 40 microns in length. The composition will usually be substantially homogenous (≧95%), mineralogically pure i.e., highly crystalline (same crystal structure) (≧90%) and substantially homogenous morphologically, generally varying by no more than ±20% from the average of each dimension.

The crystalline hydroxyapatite has a net positive charge at physiologic pH which attracts charged proteins, such as collagen or other exogenous or endogenous proteins, which may serve as growth factors, chemoattractants, and the like. Thus, the coating may provide for the presence of such products on the surface of the hydroxyapatite. The exceptionally high surface of this coating presents orders of magnitude more binding surface than the uncoated implant or the conventional calcium phosphate coatings. Specifically, it has been found that plasma sprayed HA coatings would not bind to a solution or suspension of antibiotic.

The calcium phosphate coatings may be applied to solid surfaces, porous surfaces, etched surfaces, or any other type of surface. Because the coating is applied in a liquid medium which is able to penetrate channels, pores, indentations and other structural features, a uniform coating can be obtained which can coat substantially the entire surface, without leaving exposed areas. The subject process finds particular application with devices involving fine bead layers, where the beads will be two or more layers, requiring that at least about two layers of the beads be penetrated and coated with the hydroxyapatite or its analog. Thus, penetrations are achieved in a porous substrate, such as is used in prosthesis devices, of at least about 0.5 mm, more usually at least about 1 mm.

SUMMARY OF THE INVENTION

It is an object of the invention to provide a versatile and simple method of applying therapeutic agents to a calcium phosphate surface found by precipitation prior to implantation of a coated implant.

It is yet another object of the invention to provide a simple and fast method of providing a calcium phosphate coated surface with doses of water-soluble antibiotics prior to implantation of the implant.

These and other objects are achieved by a method where applying the therapeutic agent, especially an antibiotic, to the implant comprising coating the implant with preferably at least two layers of crystalline hydroxyapatite by precipitating the hydroxyapatite or calcium phosphate from solutions. The implant is then dried and packaged. In a preferred embodiment, immediately prior to implantation, the therapeutic agent or antibiotic is added to sterile deionized water or sterile water for injection and the implant is removed from the package and at least the hydroxyapatite or calcium phosphate surface thereof is immersed in the solution.

Alternatively, the antibiotic solution or suspension can be incorporated into the dried coating prior to packaging. The surgeon can then use the as supplied implant or add an additional coating of antibiotic to the HA antibiotic coated portion of the implant.

When applied in the operating room, the therapeutic solution may be pipetted into the calcium phosphate surface. The implant is then implanted in its wetted state. Alternately, the method for providing a therapeutic agent to an implant site includes providing the packaged implant coated with crystalline calcium phosphate or crystalline hydroxyapatite and the therapeutic agent by the same process as described above prior to packaging. If done in the operating room immediately prior to implantation, the calcium phosphate or hydroxyapatite coated implant is removed from the package and coated with an aqueous solution containing the therapeutic agent such as an antibiotic or a bone morphogenic protein. This can be done by immersing the calcium phosphate or hydroxyapatite coated implant into an aqueous solution of a therapeutic agent such as, for example, an antibiotic or bone growth stimulator such as bone morphogenic protein. Alternately, the aqueous solution may be pipetted or even poured over the surface. The water and therapeutic agents may be added to the dried coating drop wise. The implant may be either implanted in the bone canal in its wet condition or allowed to dry in air prior to implantation. The therapeutic agents, such as an antibiotic, may be either dissolved in the water to form the aqueous solution or may be suspended in the water to form the aqueous mixture that is placed on the calcium phosphate hydroxyapatite coating.

Useful antibiotics for use in this method are cefamandole, tobramycin, vancomycin, penicillin, cephalosporin C, cephalexin, cefaclor, cefamandole, ciprofloxacin and bisphosphonates.

DETAILED DESCRIPTION OF THE PREFERRED EMBODIMENTS

While a single layer of calcium phosphate may be applied the preferred method involves applying at least two layers of calcium phosphate to a metallic prosthesis. The first layer is of very small crystals achieved by providing conditions which result in a high density of heterogeneous nucleation sites, so that there is a large number of hydroxyapatite nucleation sites on the substrate. This is preferably followed by at least one additional coating under conditions that provide for a lower level of nucleation modulated crystal growth, so as to produce substantially larger crystals. Desirably, one or more additional coating layers are provided, where the conditions are the same or at even lower levels of nucleation than the second coating to produce larger size crystals as compared to the second coating. Usually, there will be not more than five coatings, preferably not more than about three coatings.

The first layer will generally be of a thickness in a range of about 0.01 microns to 10 microns. The second coating will generally be of a thickness in a range of about 1 micron to 40 microns, with crystals of a size in the length range of about 0.01 microns to 20 microns. The third and successive coatings will generally range as to each layer of a thickness in a range of about 1 micron to 40 microns, preferably about 5 microns to 10 microns, having crystals of a diameter of about 0.1 to 2 microns, and a length of about 1 to 10 microns, preferably about 0.1 to 1 micron in diameter, and a length of about 2 microns to 7 microns. The total thickness of the second and succeeding layers will generally be in the range of about 5 microns to 20 microns.

The various layers can be achieved, by varying the concentration of the reactants, the pH, temperature, manner of combining the reactants in the reactor, nature of the liquid flow, and the like. Preferably, the reactants and substrate will move in relation to one another, so that the substrate is continuously encountering a specific reaction mixture. Conveniently, the reaction mixture may be streamed past the substrate, using laminar or turbulent flow, preferably turbulent flow, either by providing for a tubular reactor with a reaction mixture which may be recycled and spent ingredients replenished, or by using a mixer, where the portion of the substrate to be coated is positioned at a site displaced from the center of the reactor and the reaction mixture continuously agitated with a stream flowing around the walls or the like. The specific conditions for the reaction mixture are determined by the flow conditions determined by reactant concentration, geometry of combination, fluid flow regime, vessel geometry, and the like. If desired, these conditions can be varied in a manner that allows the coating to be applied in one step.

To obtain the coating, vitallium (Co—Cr) or titanium implants are carefully cleaned and optionally passivated and introduced into a stainless steel processing tank comprising a 10% by weight ammonium acetate solution in deionized water ($dh_2O$). The implants are placed downstream from calcium and phosphate addition ports and rapidly agitated. The stainless steel tank is covered with a protective lid to reduce evaporative heat loss. When the ammonium acetate solution has been heated to 80° C., the pH monitored, so that the solution is maintained at 80° C. and ph 7.4. The coating process is begun when the temperature reached 80.0° C. and the solution was at pH 7.4. These conditions were maintained throughout the coating process.

Addition of the reactants, which preferably are 0.5M calcium acetate and 0.3M ammonium phosphate monobasic, is then begun at a rate to provide the desired calcium to phosphate ratio, while maintaining the pH by the addition of concentrated ammonium hydroxide. The addition is carried out over a period of two to four hours. The addition rate is varied to produce the desired thickness of coating.

The implant substrate may then be removed, washed and allowed to air dry. It may also be hot air dried. When the coating process is finished, the coatings are visually inspected for coating coverage and quality. If coating coverage or quality is unacceptable the coating may be removed and the process repeated. A description of this process may be found in the article "A Novel Method For Solution Deposition Of Hydroxyapatite On To Three Dimensionally Porous Metallic Surfaces: Peri-Apatite HA," Mat. Res. Soc. Symp. Proc. Vol. 599, 2000 Material Research Society.

Once the crystalline coating has been applied to the prosthesis, the prosthesis is air dried, packaged and sterilized. The sterilized package implant is then ready for use in the operating room. Since the implant is not precoated with an antibiotic or other therapeutic agent such as Bone Morphogenic protein (BMP), the surgeon can determine at the time of surgery whether an antibiotic or other agent is needed at all and, if so, what type of antibiotic or other agent would be best suited. The surgeon then uses the method of the present invention.

Because of the difference in surface area and surface energy between the non-crystalline plasma calcium phosphate coated implants and the implants in which the hydroxyapatite is precipitated from solution, the latter will readily absorb the water and antibiotic combination mixed by the surgeon at the time of surgery or mixed and applied prior to packaging. While any antibiotic or therapeutic agent may be used, whether water-soluble or in a suspension, the following examples illustrate a variety of antibiotics with various zones of inhibition (in millimeters) for infections indicated.

TABLE I

| Antibiotic | Salt | Zone of Inhibition (mm) |
| --- | --- | --- |
| Tobramycin | Sulfate | 10 |
| Vancomycin | Hydrochloride | 10.5 |
| Penicillin | Sodium Salt | 28 |
| Penicillin | Potassium Salt | 29 |
| Penicillin | Procaine | 26.5 |
| Penicillin | Benzathine | 22.5 |
| Cephalosporin C | Zinc Salt | 11.5 |
| Cephalexin | Hydrate | 19 |
| Cefaclor | Monohydrate | 20.5 |
| Cefamandole | Naftate | 25 |
| Ciprofloxacin | Hydrochloride | 15.5 |

Eleven antibiotics were used to overcome any concerns that there may be ionic interactions between the various salts (used to stabilize different antibiotics) and the calcium phosphate coating.

In all the tests, the results show that various antibiotics can be effectively incorporated into the precipitated crystalline coating and will be released rapidly at effective concentrations. There appears to be no interaction between the antibiotic salts and hydroxyapatite coatings that would bind the antibiotic to the coating, thereby preventing release.

The results are clinically significant because the proposed method will allow surgeons to prepare individual therapies for cultured bacteria at the time of revision or other surgery. The method does not preclude the use of thermally sensitive antibiotics, as would be the case when using exothermic bone cement as a carrier.

EXAMPLE I 1.2 Grams of tobramycin sulfate was dissolved in 12 milliliters of sterile deionized water (100 mg/ml). Implants in the form of 12 mm diameter test coupons were of titanium that had been coated with crystalline hydroxyapatite as applied by the method of U.S. Pat. No. 5,164,187 were provided. Ten (10) $\mu$l of solution was pipetted onto the surface of each of the peripatetic (HA) coated disks and allowed to dry. Application of the liquid antibiotic solution or suspension can be performed via pipetting or using a syringe rather than immersion, which does not allow the same level of control of the therapeutic dosing. The test coupons were then placed into a buffered saline at 37° C. immediately after the absorption process was completed. It was determined that all the antibiotic was released into the buffered saline solution within twenty-four hours of immersion. Additional testing in the form of a modified Kirby Bauer susceptibility model was performed which showed that the released antibiotic remained biologically active and thus, was not affected by the absorption into the hydroxyapatite structure. In the well-known Kirby Bauer Susceptibility Model test organisms were propagated and handled in accordance with ATCC recommendations for broth media, agar, and incubation specifications. *Staphylococcus aureus* (ATCC strain #6538) was prepared by inoculating trypticase soy broth TSB and incubating at 37° C. for 24 hr. Microbial suspensions were adjusted to an absorbency of 0.325 using a spectrophotometer (wavelength=475nm) and swabbed onto Mueller-Hinton agar plates. Each seeded plate was challenged with both an antibiotic containing HA disk and a non-antibiotic containing HA disk, which served as a control. Samples were tested in duplicate (i.e., two plates per organism). Following incubation for 24 hr. at 37° C., the plates were examined for zones of inhibition around the disks. The zone of inhibition is defined as the distance between the test disk and the edge of bacterial growth. It is common for a hazy, or "ghost" zone to exist between the areas of complete inhibition and full bacterial growth. This "ghost" zone is the result of partial inhibition and is not included in the measurement of the zone of inhibition. As a comparison, untreated test coupons coated with hydroxyapatite but not immersed in the antibiotic solution exhibited no antibacterial properties.

While the therapeutic solution was pipetted onto the surface the test coupon could have just as easily been applied by a syringe or immersed in the solution. If necessary, a series of applications of the therapeutic agents/drying can be done to increase the concentration of the agents.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of applying coating having a therapeutic agent to an implant comprising:
   coating the implant with a layer of crystalline hydroxyapatite by precipitating the hydroxyapatite from solution;
   drying the coated implant,
   sterilizing the coated implant;
   packaging the coated implant;
   then adding a desired therapeutic agent to water;
   removing the implant from the package and then coating the implant with the water and therapeutic agent; and thereafter implanting the implant coated with the therapeutic agent.

2. The method as set forth in claim 1 further including implanting the implant in its wetted state.

3. The method as set forth in claim 1 wherein the therapeutic agent is dissolved in the water.

4. The method as set forth in claim 1 wherein the therapeutic agent is suspended in the water.

5. The method as set forth in claim 1 wherein the therapeutic agent is an antibiotic.

6. The method as set forth in claim 5 wherein the antibiotic is selected from the group consisting of Tobramycin, Vancomycin, Penicillin, Cephalosporin C, Cephalexin, Cefaclor, Cefamandole, Bisphosphonates and Ciprofloxacin and a combination thereof.

7. The method as set forth in claim 1 wherein the implant is immersed in the water and therapeutic agent.

8. The method as set forth in claim 1 wherein the water and therapeutic agent are added to the dried coating drop wise.

9. The method as set forth in claim 1 wherein the hydroxyapatite coating comprises at least two layers.

10. A method for providing a therapeutic agent to an implant comprising:
   providing an implant having a dry coating of crystalline calcium phosphate minerals;
   packaging the implant;
   sterilizing the implant;
   removing the implant from the package;
   coating the crystalline calcium phosphate implant after removing it from the package with an aqueous solution of a therapeutic agent by adding the solution to the dried coating drop wise; and
   immediately implanting the implant coated with the solution of the therapeutic agent.

11. The method as set forth in claim 10 wherein the therapeutic agent is dissolved in the water.

12. The method as set forth in claim 10 wherein the therapeutic agent is suspended in the water.

13. The method as set forth in claim 10 wherein the therapeutic agent is an antibiotic.

14. The method as set forth in claim 13 wherein the antibiotic is selected from the group consisting of Tobramycin, Vancomycin, Penicillin, Cephalosporin C, Cephalexin, Cefaclor, Cefamandole and Ciprofloxacin and a combination thereof.

15. The method as set forth in claim 10 wherein the implant is immersed in the aqueous solution of a therapeutic agent.

16. The method as set forth in claim 15 wherein the coating of crystalline calcium phosphate has more than one layer.

17. A method of applying a coating having a therapeutic agent to an implant comprising:
   coating the implant with a layer of hydroxyapatite by precipitating the hydroxyapatite from solution;
   drying the coated implant;
   packaging the coated dried implant; sterilizing the packaged coated implant;
   mixing a desired therapeutic agent with water;
   removing the dried implant from the package;
   coating the dried hydroxyapatite coated implant with the water and therapeutic agent; and
   immediately implanting the implant after coating it with the water and therapeutic agent.

18. The method as set forth in claim 17 further including implanting the implant in its wetted state.

19. The method as set forth in claim 17 wherein the therapeutic agent is dissolved in the water.

20. The method as set forth in claim 17 wherein the therapeutic agent is suspended in the water.

21. The method as set forth in claim 17 wherein the therapeutic agent is an antibiotic.

22. The method as set forth in claim 21 wherein the antibiotic is selected from the group consisting of Tobramycin, Vancomycin, Penicillin, Cephalosporin C, Cephalexin, Cefaclor, Cefamandole, Bisphosphonates and Ciprofloxacin and a combination thereof.

23. The method as set forth in claim 17 wherein the implant is immersed in the water and therapeutic agent.

24. The method as set forth in claim 17 wherein the water and therapeutic agent are added to the dried coating drop wise.

25. The method as set forth in claim 17 wherein the hydroxyapatite coating is comprises at least two layers.

* * * * *

UNITED STATES PATENT AND TRADEMARK OFFICE
CERTIFICATE OF CORRECTION

PATENT NO. : 6,596,338 B2
DATED : July 22, 2003
INVENTOR(S) : Christopher Scott, Joseph Zitelli and Paul Higham It is certified that error appears in the above-identified patent and that said Letters Patent is hereby corrected as shown below:

Column 6,
Line 64, before "packaging" insert -- then --.

Column 8,
Line 15, "coated dried" should read -- dried coated --.

Signed and Sealed this

Second Day of December, 2003

JAMES E. ROGAN
*Director of the United States Patent and Trademark Office*